United States Patent
Kobayashi et al.

(10) Patent No.: US 12,108,166 B2
(45) Date of Patent: Oct. 1, 2024

(54) ENDOSCOPE SYSTEM

(71) Applicant: OLYMPUS CORPORATION, Hachioji (JP)

(72) Inventors: Yuichiro Kobayashi, Koganei (JP); Yusuke Yamamoto, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 308 days.

(21) Appl. No.: 17/839,660

(22) Filed: Jun. 14, 2022

(65) Prior Publication Data

US 2022/0311911 A1    Sep. 29, 2022

Related U.S. Application Data

(63) Continuation of application No. PCT/JP2019/050080, filed on Dec. 20, 2019.

(51) Int. Cl.
    *H04N 23/81*    (2023.01)
    *A61B 1/00*    (2006.01)
    *A61B 1/045*    (2006.01)

(52) U.S. Cl.
    CPC ....... *H04N 23/81* (2023.01); *A61B 1/000095* (2022.02); *A61B 1/00114* (2013.01); *A61B 1/045* (2013.01)

(58) Field of Classification Search
    CPC .................. H04N 23/81; H04N 23/555; A61B 1/000095; A61B 1/00114; A61B 1/045; A61B 1/00006; A61B 1/05; A61B 1/018
    See application file for complete search history.

(56) References Cited

U.S. PATENT DOCUMENTS

2020/0357098 A1*  11/2020  Yoo ................. G16H 50/20
2021/0052226 A1*  2/2021  Jauss ................ A61B 5/7214

FOREIGN PATENT DOCUMENTS

| JP | 59-69044 A | 4/1984 |
| JP | 2-136122 A | 5/1990 |
| JP | 11-318909 A | 11/1999 |
| JP | 2013-17752 A | 1/2013 |

OTHER PUBLICATIONS

International Search Report dated Feb. 10, 2020, issued in counterpart International Application No. PCT/JP2019/050080, w/English translation (4 pages).

* cited by examiner

*Primary Examiner* — Kyu Chae
(74) *Attorney, Agent, or Firm* — WHDA, LLP (57) ABSTRACT

In an endoscope system, an imaging device is electrically connected to a signal line and is configured to output a video signal to the signal line. A receiver circuit is electrically connected to the signal line and is configured to receive the video signal. A noise detection circuit is configured to detect that noise having a higher frequency than a frequency of the video signal is mixed into the video signal. A filter circuit has a function of reducing the noise included in the video signal. An imaging control circuit is configured to set a signal-output time per one pixel of the imaging device to a second set time longer than a first set time and a filter control circuit is configured to turn on the function of the filter circuit when the noise is detected by the noise detection circuit.

14 Claims, 7 Drawing Sheets

PRIOR ART

FIG. 7

PRIOR ART

ENDOSCOPE SYSTEM

The present application is a continuation application based on International Patent Application No. PCT/JP2019/050080 filed on Dec. 20, 2019, the content of which is incorporated herein by reference.

BACKGROUND OF THE INVENTION

Field of the Invention

The present invention relates to an endoscope system.

Description of Related Art

Figure 6:
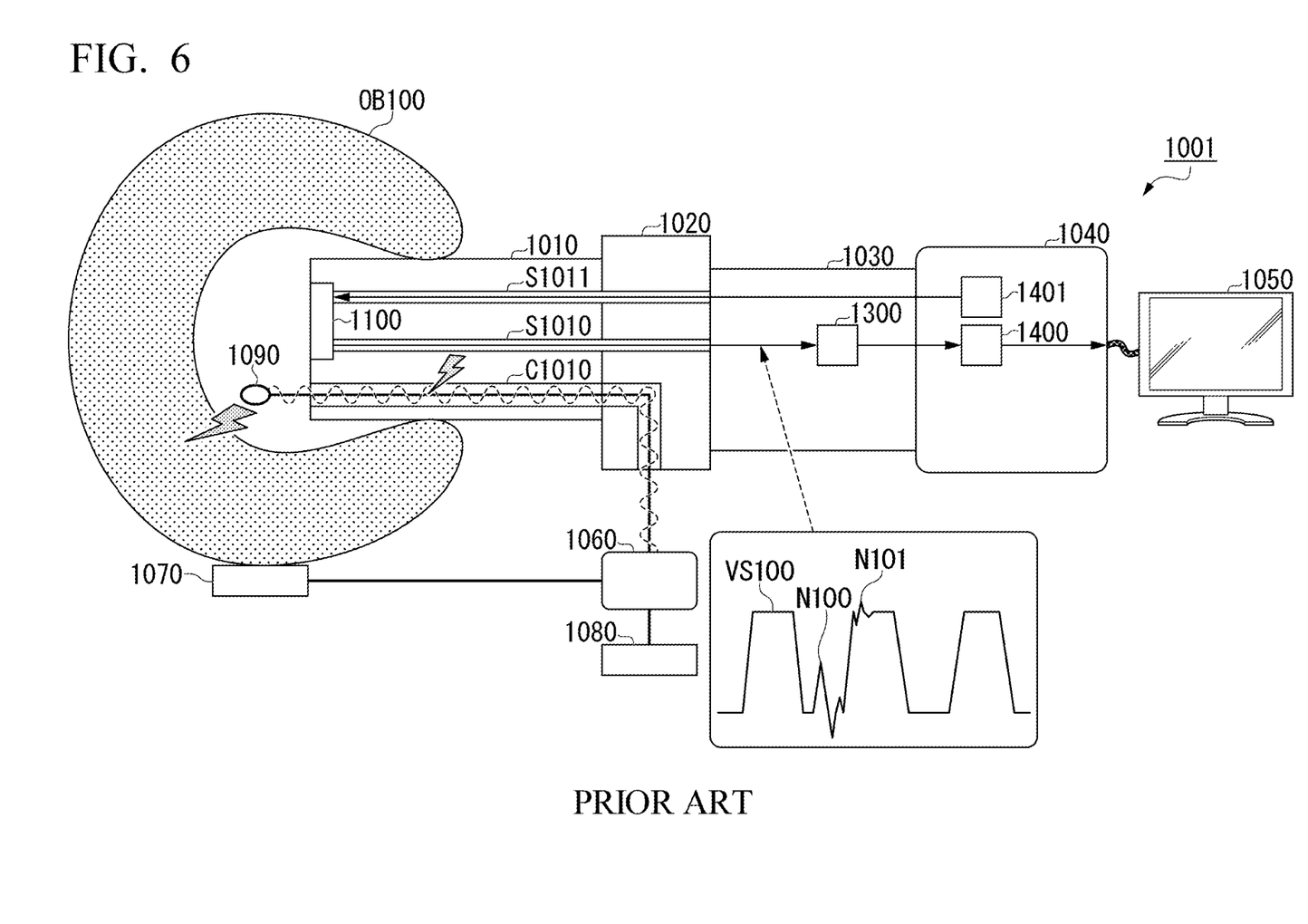
FIG. 6 is a block diagram showing a configuration of an endoscope system of the prior art.

FIG. 6 shows a configuration of an endoscope system 1001 of the prior art. The endoscope system 1001 shown in FIG. 6 includes an endoscope insertion unit 1010, an operation unit 1020, a connection unit 1030, a main body 1040, and a monitor 1050.

The endoscope insertion unit 1010 is a scope and is inserted into the inside of a subject OB100. The endoscope insertion unit 1010 includes an imaging device 1100. The imaging device 1100 is disposed in the distal end of the endoscope insertion unit 1010. The imaging device 1100 acquires an optical image of the inside of the subject OB100 and generates a video signal on the basis of the optical image. The imaging device 1100 outputs the generated video signal.

The operation unit 1020 is disposed in the rear end of the endoscope insertion unit 1010. The operation unit 1020 accepts various operations for the endoscope insertion unit 1010 from a user.

The video signal output from the imaging device 1100 is transferred to the connection unit 1030 by a signal line S1010 disposed inside the endoscope insertion unit 1010 and the operation unit 1020. The connection unit 1030 is disposed between the operation unit 1020 and the main body 1040. The connection unit 1030 includes a video-signal receiver circuit 1300. The video-signal receiver circuit 1300 receives the video signal and performs predetermined processing on the video signal.

The main body 1040 includes an image-processing circuit 1400 and an imaging control circuit 1401. The image-processing circuit 1400 performs image processing on the video signal output from the video-signal receiver circuit 1300. The video signal processed by the image-processing circuit 1400 is output to the monitor 1050. The monitor 1050 displays a video on the basis of the video signal. Observation of the subject OB100 is performed on the basis of the displayed video. The imaging control circuit 1401 outputs a control signal for controlling an imaging device 1100. The control signal output from the imaging control circuit 1401 is transferred to the imaging device 1100 by a signal line S1011 disposed inside the endoscope insertion unit 1010 and the operation unit 1020.

When treatment of a lesion is performed, a high-frequency-signal generation device such as an electrosurgical knife device is used. The treatment of a lesion is cutting, hemostasis, or the like. In FIG. 6, an example in which an electrosurgical knife device 1060, a counter electrode plate 1070, a foot switch 1080, and a snare 1090 are used is shown. The snare 1090 is a treatment tool and is inserted into the inside of the subject OB100 through a channel C1010 disposed inside the endoscope insertion unit 1010 and the operation unit 1020. The electrosurgical knife device 1060 is driven when the snare 1090 protrudes from the distal end of the endoscope insertion unit 1010. The counter electrode plate 1070 is attached to the subject OB100. A user drives the electrosurgical knife device 1060 by operating the foot switch 1080.

The electrosurgical knife device 1060 generates a high-frequency signal and transmits the high-frequency signal to the snare 1090. When the high-frequency signal flows in the snare 1090, high-frequency noise is transmitted to the signal line S1010. Therefore, high-frequency noise N100 and high-frequency noise N101 are mixed into a video signal VS100 that flows in the signal line S1010. When a video is displayed on the basis of the video signal into which high-frequency noise is mixed, noise appears in the video. Hereinafter, noise that appears in a video is described as image noise.

Image noise caused by high-frequency noise is mainly classified into two types of noise. The two types of noise are bright-spot image noise and belt-like or banding image noise. The high-frequency noise includes components having a frequency of several hundred MHz or more (for example, 200 MHz or more). It is known that bright-spot image noise is generated in a case in which a timing based on these components matches a sampling timing of an A/D conversion circuit (analog-to-digital conversion circuit).

Considering the above-described circumstances, disposing a low-pass filter circuit on a signal line of a video signal for reducing high-frequency noise is proposed. In this way, bright-spot image noise is expected to be reduced. For example, a device disclosed in Japanese Unexamined Patent Application. First Publication No. H2-136122 turns on a noise filter when a noise detection circuit detects high-frequency noise caused by an operation of an electric scalpel.

SUMMARY OF THE INVENTION

According to a first aspect of the present invention, an endoscope system includes an imaging device, a receiver circuit, a noise detection circuit, a filter circuit, an imaging control circuit, and a filter control circuit. The imaging device is electrically connected to a signal line and is configured to output a video signal to the signal line. The receiver circuit is electrically connected to the signal line and is configured to receive the video signal. The noise detection circuit is configured to detect that noise having a higher frequency than a frequency of the video signal is mixed into the video signal. The filter circuit has a function of reducing the noise included in the video signal. The imaging control circuit is configured to set a signal-output time per one pixel of the imaging device to a first set time when the noise is not detected by the noise detection circuit. The imaging control circuit is configured to set the signal-output time to a second set time longer than the first set time when the noise is detected by the noise detection circuit. The filter control circuit is configured to turn off the function when the noise is not detected by the noise detection circuit. The filter control circuit is configured to turn on the function when the noise is detected by the noise detection circuit.

According to a second aspect of the present invention, in the first aspect, the noise detection circuit may be configured to detect that the noise is mixed into the video signal that passes between the imaging device and the filter circuit.

According to a third aspect of the present invention, in the second aspect, the noise detection circuit may be configured to compare an electric potential of one of the video signal in a blanking period and the video signal output from an optical black region in the imaging device with a predetermined value so as to determine whether the noise is mixed into the video signal.

According to a fourth aspect of the present invention, in the third aspect, the imaging control circuit may be configured to output timing information indicating one of a timing of the blanking period and a timing at which the video signal is output from the optical black region. The noise detection circuit may be configured to compare the electric potential of the video signal with the predetermined value at a timing indicated by the timing information.

According to a fifth aspect of the present invention, in the fourth aspect, the imaging control circuit may be configured to update the timing information on the basis of a frame rate of the video signal.

According to a sixth aspect of the present invention, in the second aspect, the video signal may be a differential signal including a first video signal and a second video signal having different electric potentials. The receiver circuit may be configured to convert the first video signal and the second video signal into a single-ended signal. The filter circuit may be configured to reduce the noise included in the single-ended signal. The noise detection circuit may be configured to detect that the noise is mixed into the single-ended signal.

According to a seventh aspect of the present invention, in the first aspect, the noise detection circuit may be configured to detect that the noise is mixed into the video signal that has passed through the filter circuit.

According to an eighth aspect of the present invention, in the seventh aspect, the noise detection circuit may be configured to compare an electric potential of one of the video signal in a blanking period and the video signal output from an optical black region in the imaging device with a predetermined value so as to determine whether the noise is mixed into the video signal.

According to a ninth aspect of the present invention, in the eighth aspect, the imaging control circuit may be configured to output timing information indicating one of a timing of the blanking period and a timing at which the video signal is output from the optical black region. The noise detection circuit may be configured to compare the electric potential of the video signal with the predetermined value at a timing indicated by the timing information.

According to a tenth aspect of the present invention, in the ninth aspect, the imaging control circuit may be configured to update the timing information on the basis of a frame rate of the video signal.

According to an eleventh aspect of the present invention, in the seventh aspect, the filter control circuit may be configured to turn off the function in a period during which the noise detection circuit detects that the noise is mixed into the video signal.

According to a twelfth aspect of the present invention, in the first aspect, the imaging control circuit may be configured to reduce a frame rate of the video signal in the imaging device so as to set the signal-output time to the second set time when the noise is detected by the noise detection circuit.

According to a thirteenth aspect of the present invention, in the first aspect, the imaging device may be configured to generate the video signal on the basis of a pixel signal that is read from each of two or more pixels that generate the pixel signals. The imaging control circuit may be configured to thin out a pixel from which the pixel signal is read among the two or more pixels in the imaging device so as to set the signal-output time to the second set time when the noise is detected by the noise detection circuit.

According to a fourteenth aspect of the present invention, in the first aspect, the noise detection circuit may be configured to determine a frequency of the noise. The filter circuit may be configured such that a cut-off frequency thereof is variable. The filter control circuit may be configured to set the cut-off frequency on the basis of the frequency determined by the noise detection circuit.

DETAILED DESCRIPTION OF THE INVENTION

As described above, high-frequency noise includes components having a frequency of several hundred MHz or more (for example, 200 MHz or more). This frequency is defined as fn, and it is assumed that a low-pass filter that cuts off components having a higher frequency than fn is disposed. When the cut-off frequency of the low-pass filter is defined as fc, the frequency fn is higher than the cut-off frequency fc of the low-pass filter. In addition to these, a required time for an imaging device to output a video signal of one pixel is defined as Ts, and the frequency of the video signal is defined as fs. The frequency fs is equal to 1/Ts. In order to significantly attenuate the high-frequency noise mixed into the video signal and suppress deterioration of the waveform of the video signal, a relationship indicated by the following Expression (A) needs to be established. The constant C in Expression (A) is about ten.

$$fc \geq C/Ts \qquad (A)$$

An imaging device used in an endoscope system in recent years features a large number of pixels and a video signal with a high frame rate. As the number of pixels increases, the resolution of the video signal increases. As the frame rate of the video signal increases, movement of a subject in a video becomes smooth. Therefore, a time Ts per one pixel in the video signal is shortened, in other words, the frequency fs tends to increase. In addition, the frequency fn of high-frequency components included in the high-frequency noise does not depend on the frequency fs of the video signal. Therefore, there is a case in which the relationship indicated by the Expression (A) is not established.

Figure 7:
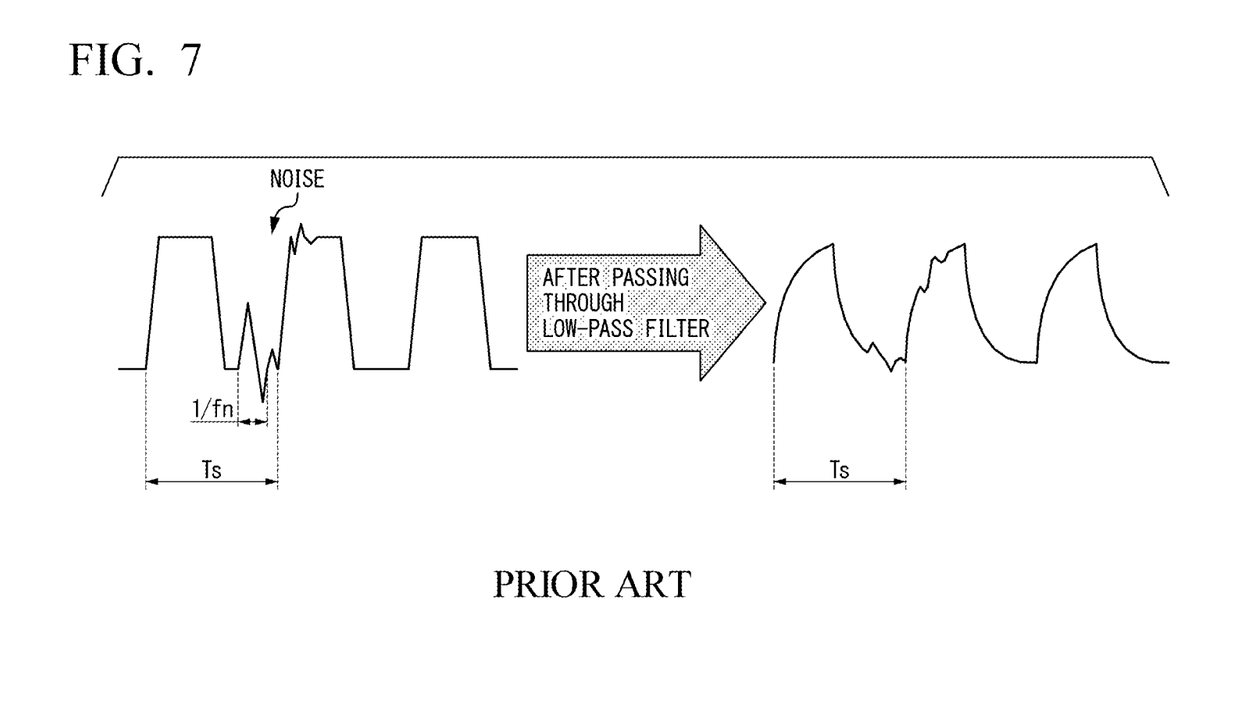
FIG. 7 is a timing chart showing a waveform of a video signal in the prior art.

In a case in which the relationship indicated by the Expression (A) is not established in the prior art, the waveform of the video signal passing through the low-pass filter deteriorates as shown in FIG. 7. Therefore, a different value from an original value of the video signal is received by a video-signal receiver circuit, and a video signal having a false value is generated. In consequence, the image quality of a subject including a lesion deteriorates in a video displayed on a monitor.

Hereinafter, embodiments of the present invention will be described with reference to the drawings.

First Embodiment

Figure 1:
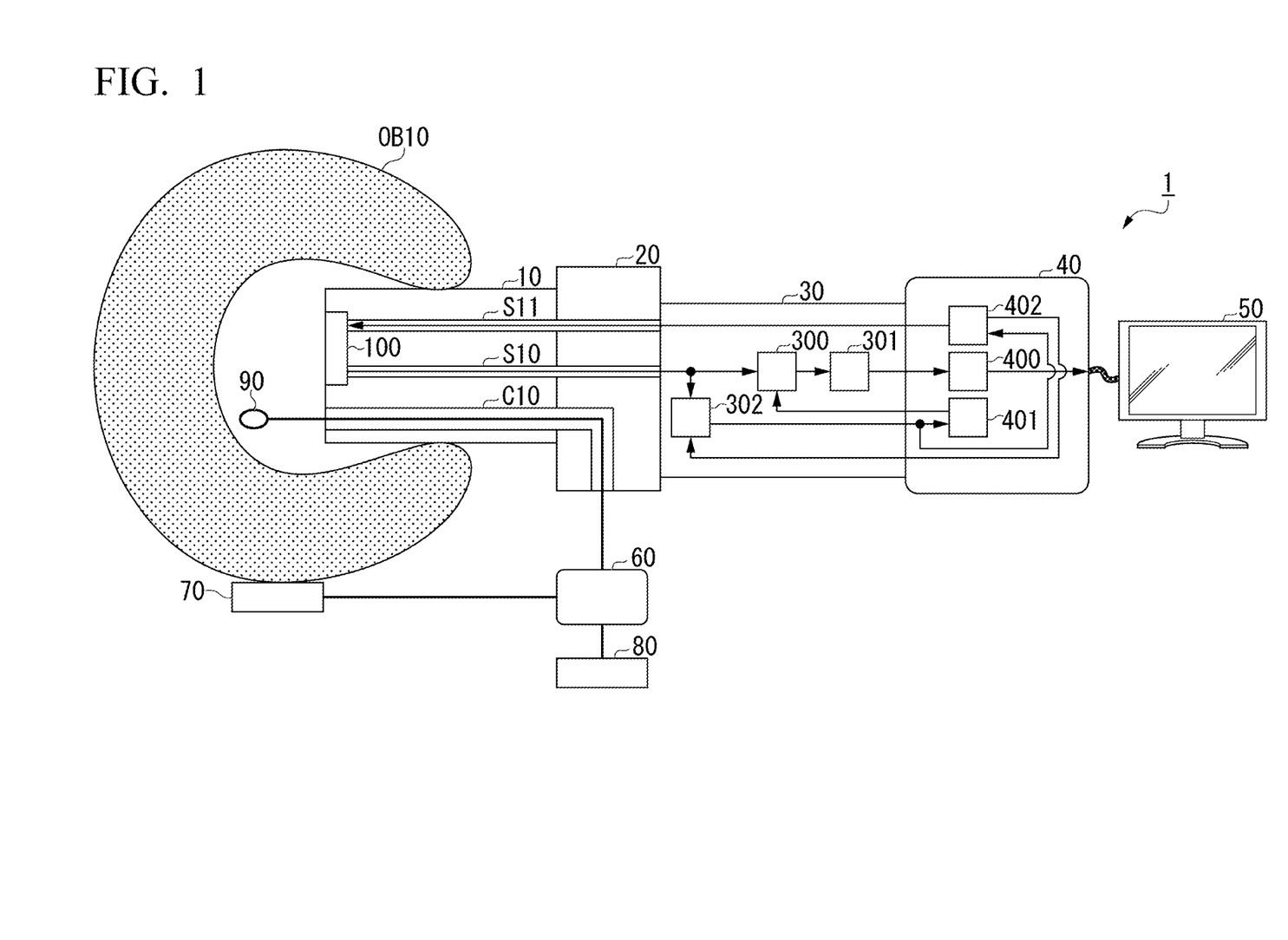
FIG. 1 is a block diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 10, an operation unit 20, a connection unit 30, a main body 40, and a monitor 50. The endoscope insertion unit 10 includes an imaging device 100. The connection unit 30 includes a low-pass filter circuit 300, a video-signal receiver circuit 301, and a noise detection circuit 302. The main body 40 includes an image-processing circuit 400, a filter control circuit 401, and an imaging control circuit 402.

A schematic configuration of the endoscope system 1 will be described. The imaging device 100 is electrically connected to a signal line S10 and outputs a video signal to the signal line S10. The video-signal receiver circuit 301 is electrically connected to the signal line S10 and receives the video signal. The noise detection circuit 302 detects that noise having a higher frequency than the frequency of the video signal is mixed into the video signal. Hereinafter, this noise is described as high-frequency noise. The frequency of any component included in the high-frequency noise is higher than that of any component included in the video signal. The low-pass filter circuit 300 reduces the high-frequency noise included in the video signal. The imaging control circuit 402 sets a signal-output time per one pixel of the imaging device 100 to a first set time when the high-frequency noise is not detected by the noise detection circuit 302. The imaging control circuit 402 sets the signal-output time per one pixel of the imaging device 100 to a second set time longer than the first set time when the high-frequency noise is detected by the noise detection circuit 302. The filter control circuit 401 turns off the function of the low-pass filter circuit 30) when the high-frequency noise is not detected by the noise detection circuit 302. The filter control circuit 401 turns on the function of the low-pass filter circuit 300 when the high-frequency noise is detected by the noise detection circuit 302.

A detailed configuration of the endoscope system 1 will be described. The endoscope insertion unit 10 is a scope and is inserted into a subject OB10. The imaging device 100 is disposed in the distal end of the endoscope insertion unit 10. The imaging device 100 is an image sensor such as a charge-coupled device (CCD) or a complementary metal-oxide-semiconductor (CMOS).

The imaging device 100 acquires an optical image of the inside of the subject OB10 and generates a video signal on the basis of the optical image. The imaging device 100 outputs the generated video signal. The imaging device 100 includes two or more pixels not shown in FIG. 1. The imaging device 100 generates a video signal on the basis of a pixel signal that is read from each of the two or more pixels that generate the pixel signals. Hereinafter, an example in which the video signal is an analog signal will be described. In one or more embodiments of the present invention, the video signal may be a digital signal.

The operation unit 20 is disposed in the rear end of the endoscope insertion unit 10. The operation unit 20 accepts various operations for the endoscope insertion unit 10 from a user.

The video signal output from the imaging device 100 is transferred to the connection unit 30 by the signal line S10 disposed inside the endoscope insertion unit 10 and the operation unit 20. The connection unit 30 is disposed between the operation unit 20 and the main body 40.

The low-pass filter circuit 300 is electrically connected to the signal line S10. The low-pass filter circuit 300 is disposed between the imaging device 100 and the video-signal receiver circuit 301 in a transmission path of the video signal. The video signal output from the imaging device 100 is input into the low-pass filter circuit 3K). The state of the low-pass filter circuit 300 is set to one of an on-state and an off-state. The state of the low-pass filter circuit 300 can be switched between the on-state and the off-state.

When the state of the low-pass filter circuit 300 is the on-state, the low-pass filter circuit 300 cuts off a signal having a higher frequency than a cut-off frequency fc and transmits a signal having a frequency lower than or equal to the cut-off frequency fc. Since the frequency fn (for example, 200 MHz or more) of the high-frequency noise is higher than the cut-off frequency fc, the high-frequency noise in the video signal is reduced. The low-pass filter circuit 300 outputs the video signal in which the high-frequency noise is reduced to the video-signal receiver circuit 301. When the state of the low-pass filter circuit 300 is the off-state, the low-pass filter circuit 300 stops the function of cutting off a signal having a higher frequency than the cut-off frequency fc. The low-pass filter circuit 300 outputs the video signal output from the imaging device 100 to the video-signal receiver circuit 301.

A band-pass filter circuit may be used instead of the low-pass filter circuit 300. When the state of the band-pass filter circuit is the on-state, the band-pass filter circuit cuts off a signal having a higher frequency than the cut-off frequency fc and transmits a signal having a frequency included in a predetermined frequency band lower than or equal to the cut-off frequency fc.

The video-signal receiver circuit 301 receives the video signal output from the low-pass filter circuit 300 and performs predetermined processing on the video signal. For example, in a case in which the video signal is an analog signal, the video-signal receiver circuit 301 performs A/D conversion on the video signal, thus converting the video signal into a digital signal. The video-signal receiver circuit 301 may perform processing such as amplification on the video signal.

The noise detection circuit 302 is electrically connected to the signal line S10. The video signal output front the imaging device 100 is input into the noise detection circuit 302. The noise detection circuit 302 detects that the high-frequency noise is mixed into the video signal on the signal line S10 between the imaging device 100 and the low-pass filter circuit 30). In other words, the noise detection circuit 302 detects that the high-frequency noise is mixed into the video signal that passes between the imaging device 100 and the low-pass filter circuit 300. The noise detection circuit 302 determines whether the high-frequency noise is mixed into the video signal, and notifies the filter control circuit 401 and the imaging control circuit 402 of a determination result.

For example, the noise detection circuit 302 determines whether the high-frequency noise is mixed into the video signal on the basis of a signal value other than a signal value of an effective pixel of the imaging device 100. Specifically, the noise detection circuit 302 compares the electric potential of one of the video signal in a blanking period and the video signal output from an optical black region in the imaging device 100 with a predetermined value, thus determining whether the high-frequency noise is mixed into the video signal. The blanking period is a horizontal blanking period or a vertical blanking period. The optical black region includes a pixel other than the effective pixel in the imaging device 100. For example, a plurality of pixels are disposed in the pixel region, the effective pixel is disposed in the center part of the pixel region, and the optical black region is disposed around the center part.

Timing information indicating one of a timing of the blanking period and a timing at which the video signal is output from the optical black region is output from the imaging control circuit 402. The noise detection circuit 302 compares the electric potential of the video signal with the predetermined value at the timing indicated by the timing information. When the timing information indicating the timing of the blanking period is output from the imaging control circuit 402, the noise detection circuit 302 compares the electric potential of the video signal in the blanking period with the predetermined value. When the timing information indicating the timing at which the video signal is output from the optical black region is output from the imaging control circuit 402, the noise detection circuit 302 compares the electric potential of the video signal output from the optical black region with the predetermined value.

When the high-frequency noise is not mixed into the video signal, the electric potential of the video signal in the blanking period and the electric potential of the video signal output from the optical black region have a known value. When the high-frequency noise is mixed into the video signal, the electric potential of the video signal in the blanking period and the electric potential of the video signal output from the optical black region have a different value from the known value. The noise detection circuit 302 can determine whether the high-frequency noise is mixed into the video signal by comparing the electric potential of the video signal with the predetermined value.

The low-pass filter circuit 300 may be disposed in the operation unit 20 or the main body 40. In a case in which the low-pass filter circuit 300 is disposed in the operation unit 20, the video-signal receiver circuit 301 is disposed in the operation unit 20 or the main body 40 and the noise detection circuit 302 is disposed in the operation unit 20. In a case in which the low-pass filter circuit 300 is disposed in the main body 40, the video-signal receiver circuit 301 is disposed in the main body 40 and the noise detection circuit 302 is disposed in the operation unit 20 or the main body 40.

The image-processing circuit 400 performs image processing on the video signal output from the video-signal receiver circuit 301. The video signal processed by the image-processing circuit 400 is output to the monitor 50. The monitor 50 displays a video on the basis of the video signal. Observation of the subject OB10 is performed on the basis of the displayed video.

The filter control circuit 401 turns on or off the function of the low-pass filter circuit 300 on the basis of the determination result reported by the noise detection circuit 302. When the noise detection circuit 302 determines that the high-frequency noise is not mixed into the video signal, the filter control circuit 401 turns off the function of the low-pass filter circuit 300. When the noise detection circuit 302 determines that the high-frequency noise is mixed into the video signal, the filter control circuit 401 turns on the function of the low-pass filter circuit 300. The noise detection circuit 302 performs determination on the high-frequency noise in a first period. The filter control circuit 401 turns on or off the function of the low-pass filter circuit 300 in a second period immediately after the first period. The first period and the second period are the same frames or consecutive frames.

The imaging control circuit 402 outputs a control signal for controlling the imaging device 100. The control signal output from the imaging control circuit 402 is transferred to the imaging device 100 by a signal line S11 disposed inside the endoscope insertion unit 10 and the operation unit 20. In addition, the imaging control circuit 402 controls a signal-output time per one pixel of the imaging device 100 on the basis of the determination result reported by the noise detection circuit 302. As a method of calculating the signal-output time, there is a method of dividing the length of one frame period by the number of pixels from which a pixel signal is read.

When the noise detection circuit 302 determines that the high-frequency noise is not mixed into the video signal, the imaging control circuit 402 sets the signal-output time per one pixel of the imaging device 100 to a predetermined time. For example, the imaging control circuit 402 sets the signal-output time to Ts1. When the noise detection circuit 302 determines that the high-frequency noise is mixed into the video signal, the imaging control circuit 402 sets the signal-output time per one pixel of the imaging device 100 to a longer time than the predetermined time. For example, the imaging control circuit 402 sets the signal-output time to Ts2. The signal-output time Ts2 is longer than the signal-output time Ts1.

Specifically, when the high-frequency noise is detected by the noise detection circuit 302, the imaging control circuit 402 reduces the frame rate of the video signal in the imaging device 100. In this way, the frame rate of the video signal is reduced, but the number of effective pixels per one frame does not change. Alternatively, when the high-frequency noise is detected by the noise detection circuit 302, the imaging control circuit 402 thins out a pixel from which a pixel signal is read in the imaging device 100. In other words, the imaging control circuit 402 causes the imaging device 100 to read a pixel signal from only some of the two or more pixels included in the imaging device 100. In this way, the frame rate of the video signal does not change, but the number of effective pixels per one frame is reduced.

A relationship indicated by the following Expression (1) is established between the cut-off frequency fc of the low-pass filter circuit 300 and the signal-output time Ts2. A constant C in Expression (1) is about ten. Since the relationship indicated by the following Expression (1) is established, the high-frequency noise mixed into the video signal is significantly attenuated and deterioration of the waveform of the video signal is suppressed.

$$fc \geq C/Ts2 \qquad (1)$$

The imaging control circuit 402 outputs a control signal for setting the signal-output time per one pixel of the imaging device 100 to Ts1 or Ts2 to the signal line S11. The noise detection circuit 302 performs determination on the high-frequency noise in the first period. The imaging control circuit 402 sets the signal-output time per one pixel of the imaging device 100 to Ts1 or Ts2 in the second period immediately after the first period. The first period and the second period are the same frames or consecutive frames.

Figure 2:
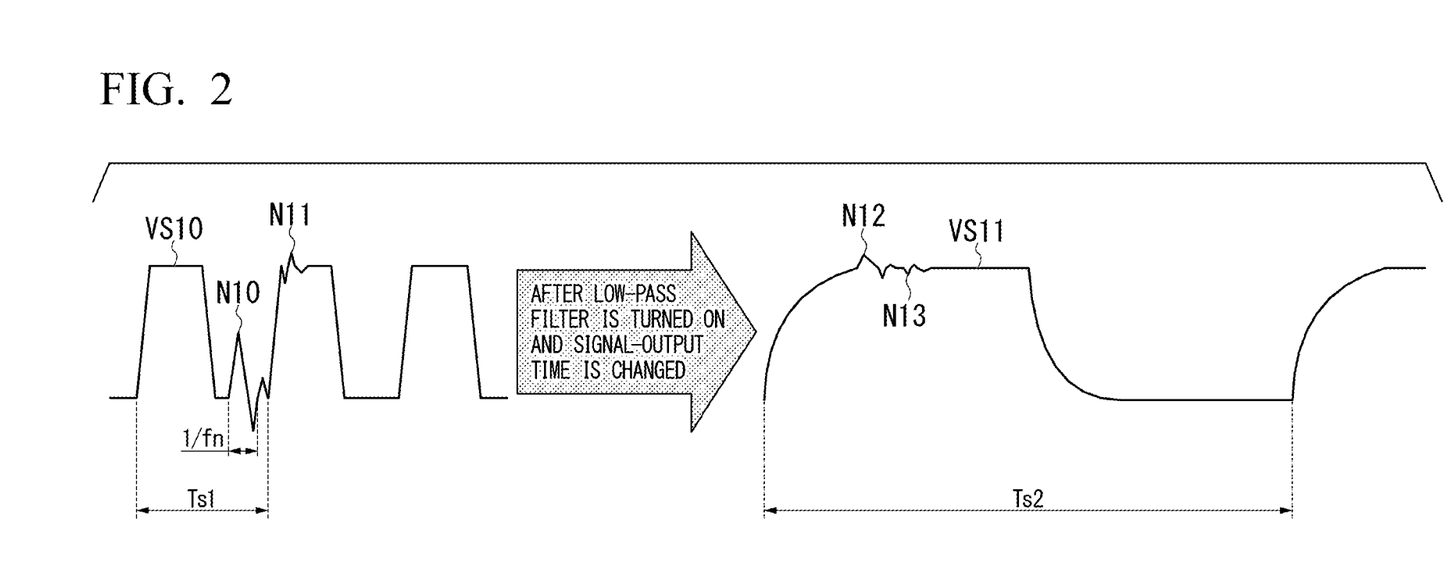
FIG. 2 is a timing chart showing a waveform of a video signal in the first embodiment of the present invention.

FIG. 2 shows the waveform of the video signal. High-frequency noise N10 and high-frequency noise N11 are mixed into a video signal VS10 that flows in the signal line S10. Since the high-frequency noise is detected by the noise detection circuit 302, the function of the low-pass filter circuit 300 is turned on and the signal-output time per one pixel of the imaging device 100 is set to Ts2. In a video signal VS11 processed by the low-pass filter circuit 300, high-frequency noise N12 and high-frequency noise N13 are significantly reduced. In addition, since the signal-output time is changed such that the relationship shown in Expression (1) is established, the original waveform of the video signal VS11 is likely to be maintained.

The control signal output from the imaging control circuit 402 is input into the imaging device 100. When the noise detection circuit 302 determines that the high-frequency noise is not mixed into the video signal, the signal-output time per one pixel of the imaging device 100 is set to Ts1 on the basis of the control signal. When the noise detection circuit 302 determines that the high-frequency noise is mixed into the video signal, the signal-output time per one pixel of the imaging device 100 is set to Ts2 on the basis of the control signal.

The imaging control circuit 402 outputs, to the noise detection circuit 302, timing information indicating one of a timing of the blanking period and a timing at which the video signal is output from the optical black region. When the imaging control circuit 402 changes the signal-output time per one pixel of the imaging device 100 by reducing the frame rate of the video signal, the above-described timing changes. Therefore, the imaging control circuit 402 updates the timing information on the basis of the frame rate of the video signal and outputs the updated timing information to the noise detection circuit 302.

In FIG. 1, an example in which an electrosurgical knife device 60, a counter electrode plate 70, a foot switch 80, and a snare 90 are used is shown. The snare 90 is a treatment tool and is inserted into the inside of the subject OB10 through a channel C10 disposed inside the endoscope insertion unit 10 and the operation unit 20. The electrosurgical knife device 60 is driven when the snare 90 protrudes from the distal end of the endoscope insertion unit 10. The counter electrode plate 70 is attached to the subject OB10. A user drives the electrosurgical knife device 60 by operating the foot switch 80.

When the electrosurgical knife device 60 is not being driven, the electrosurgical knife device 60 does not generate a high-frequency signal. Therefore, the noise detection circuit 302 determines that the high-frequency noise is not mixed into the video signal. The filter control circuit 401 turns off the function of the low-pass filter circuit 300. The imaging control circuit 402 sets the signal-output time per one pixel of the imaging device 100 to Ts1.

When the electrosurgical knife device 60 is being driven, the electrosurgical knife device 60 generates a high-frequency signal and transmits the high-frequency signal to the snare 90. When the high-frequency signal flows in the snare 90, high-frequency noise is transmitted to the signal line S10. Therefore, the high-frequency noise is mixed into the video signal that flows in the signal line S10. The noise detection circuit 302 determines that the high-frequency noise is mixed into the video signal. The filter control circuit 401 turns on the function of the low-pass filter circuit 300. The imaging control circuit 402 sets the signal-output time per one pixel of the imaging device 100 to Ts2 longer than Ts1. The low-pass filter circuit 300 reduces the high-frequency noise mixed into the video signal. Since the signal-output time is changed such that the relationship shown in Expression (1) described above is established, deterioration of the waveform of the video signal is suppressed.

The imaging device 100 may include an A/D conversion circuit. In such a case, the imaging device 100 outputs a digital video signal. In a case in which the video signal is a digital signal, the low-pass filter circuit 300, the video-signal receiver circuit 301, and the noise detection circuit 302 may be constituted by at least one of a processor and a logic circuit. Whether the video signal is an analog signal or a digital signal, the filter control circuit 401 and the imaging control circuit 402 may be constituted by at least one of a processor and a logic circuit.

For example, the processor is at least one of a central processing circuit (CPU), a digital signal processor (DSP), and a graphics-processing unit (GPU). For example, the logic circuit is at least one of an application-specific integrated circuit (ASIC) and a field-programmable gate array (FPGA). The low-pass filter circuit 300, the video-signal receiver circuit 301, the noise detection circuit 302, the filter control circuit 401, and the imaging control circuit 402 may include one or a plurality of processors. The low-pass filter circuit 300, the video-signal receiver circuit 301, the noise detection circuit 302, the filter control circuit 401, and the imaging control circuit 402 may include one or a plurality of logic circuits.

The processor may read a program and execute the read program. The program includes commands defining the operations of the processor. In other words, the functions of the processor may be realized by software. The program, for example, may be provided by using a "computer-readable storage medium" such as a flash memory. The program may be transmitted from the computer storing the program to the endoscope system 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). The functions described above may be realized by a combination of a program that has already been recorded in a computer and a differential program.

In the first embodiment, when the high-frequency noise is detected by the noise detection circuit 302, the filter control circuit 401 turns on the function of the low-pass filter circuit 300 and the imaging control circuit 402 sets the signal-output time per one pixel of the imaging device 100 to a longer time than a predetermined time. In this way, the endoscope system 1 can suppress deterioration of the waveform of the video signal.

Modified Example of First Embodiment

In a modified example of the first embodiment of the present invention, the low-pass filter circuit 300 is configured such that the cut-off frequency fc is variable. In addition, the noise detection circuit 302 is changed to a noise detection circuit 302a shown in FIG. 3. The noise detection circuit 302a has a function of determining the frequency of the high-frequency noise. The filter control circuit 401 sets the cut-off frequency fc of the low-pass filter circuit 300 on the basis of the frequency of the high-frequency noise determined by the noise detection circuit 302a.

Figure 3:
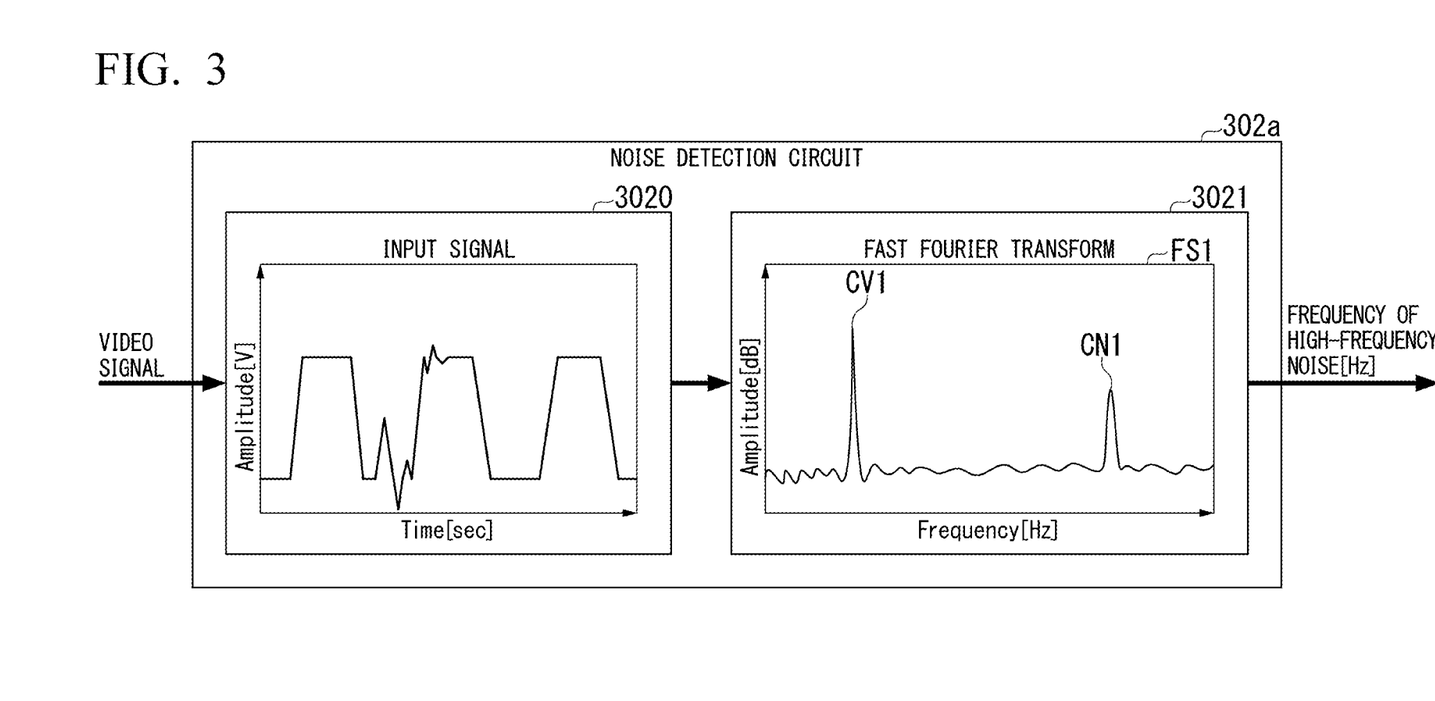
FIG. 3 is a block diagram showing a configuration of a noise detection circuit included in an endoscope system according to a modified example of the first embodiment of the present invention.

The noise detection circuit 302a includes a sampling circuit 3020 and a signal-processing circuit 3021. The sampling circuit 3020 samples a video signal at an extremely high sampling rate. The signal-processing circuit 3021 performs fast Fourier transform on the sampled signal and obtains a frequency spectrum of the components included in the video signal. The signal-processing circuit 3021 determines whether the high-frequency noise is mixed into the video signal on the basis of the frequency spectrum.

A frequency spectrum FS1 shown in FIG. 3 includes a video signal component CV1 and a high-frequency noise component CN1. Since the frequency of the video signal component CV1 is known, the signal-processing circuit 3021 can distinguish between the video signal component CV1 and the high-frequency noise component CN1. When the high-frequency noise is mixed into the video signal, the signal-processing circuit 3021 determines the frequency of the high-frequency noise. When the signal-processing circuit 3021 determines that the high-frequency noise is mixed into the video signal, the signal-processing circuit 3021 outputs information indicating the frequency of the high-frequency noise to the filter control circuit 401 and the imaging control circuit 402.

When the information indicating the frequency of the high-frequency noise is output front the noise detection circuit 302a, the filter control circuit 401 turns on the function of the low-pass filter circuit 300. In addition, the filter control circuit 401 sets the cut-off frequency fc of the low-pass filter circuit 300 to a lower frequency than that of the high-frequency noise.

When the information indicating the frequency of the high-frequency noise is output front the noise detection circuit 302a, the imaging control circuit 402 sets the signal-output time per one pixel of the imaging device 100 to Ts2 longer than Ts1. The filter control circuit 401 may notify the imaging control circuit 402 of the newly set cut-off frequency fc of the low-pass filter circuit 300, and the imaging control circuit 402 may determine whether the following Expression (2) is established. The constant C in Expression (2) is about ten.

$$fc \geq C/Ts1 \quad (2)$$

When the high-frequency noise is detected by the noise detection circuit 302a and Expression (2) is established, the imaging control circuit 402 may set the signal-output time per one pixel of the imaging device 100 to Ts1. In other words, the imaging control circuit 402 does not need to change the signal-output time. Only when the high-frequency noise is detected by the noise detection circuit 302a and Expression (2) is not established, may the imaging control circuit 402 set the signal-output time per one pixel of the imaging device 100 to Ts2.

In the modified example of the first embodiment, the endoscope system 1 can set the cut-off frequency fc of the low-pass filter circuit 300 on the basis of the frequency of the high-frequency noise.

Second Embodiment

Figure 4:
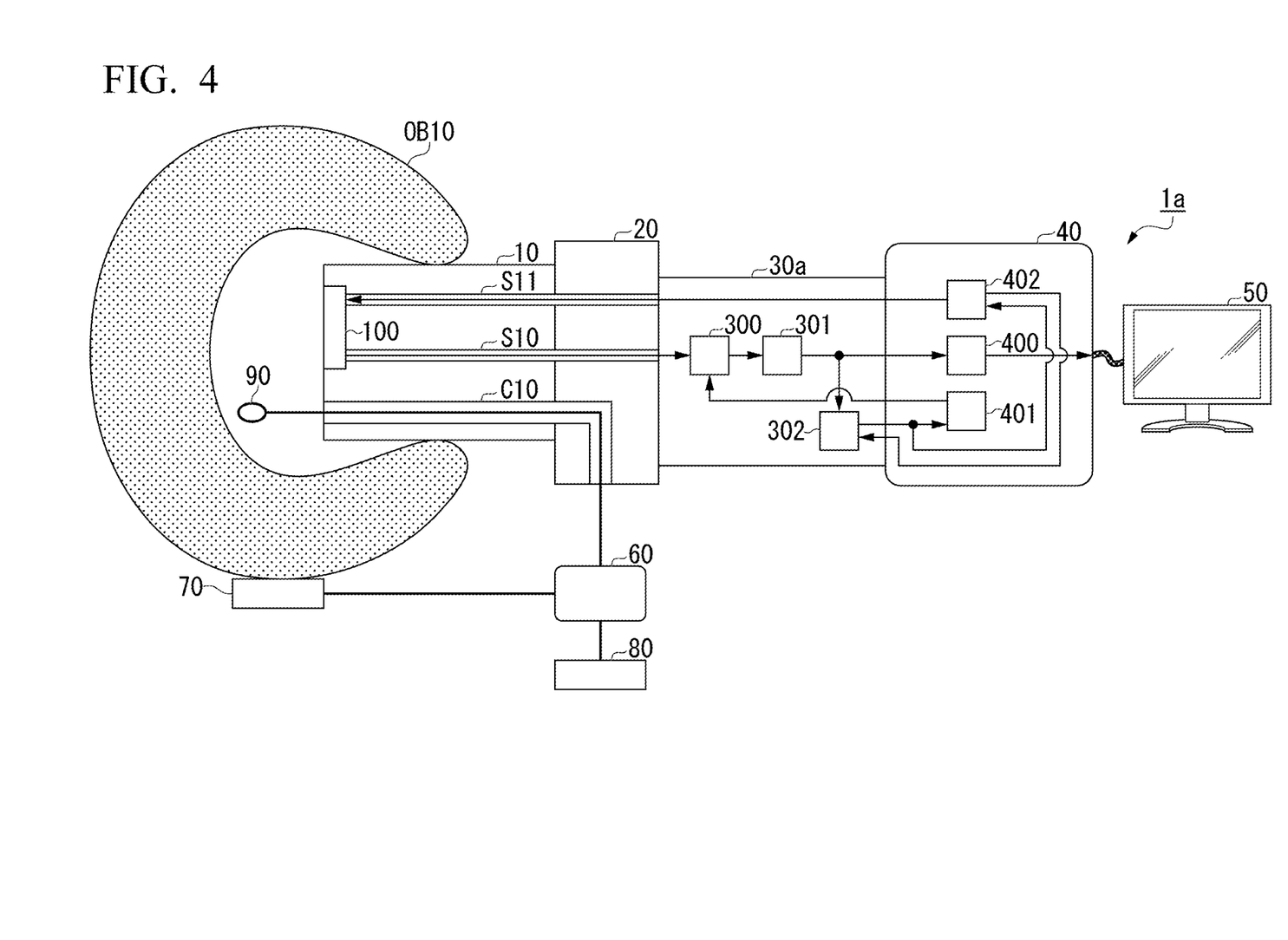
FIG. 4 is a block diagram showing a configuration of an endoscope system according to a second embodiment of the present invention.

FIG. 4 shows a configuration of an endoscope system 1a according to a second embodiment of the present invention. The same configuration as that shown in FIG. 1 will not be described.

The connection unit 30 shown in FIG. 1 is changed to a connection unit 30a. The position at which the noise detection circuit 302 shown in FIG. 4 acquires a video signal is different from that at which the noise detection circuit 302 shown in FIG. 1 acquires a video signal. The video signal output from the video-signal receiver circuit 301 is input to the noise detection circuit 302. The noise detection circuit 302 detects that the high-frequency noise is mixed into the video signal that has passed through the low-pass filter circuit 300.

In a state in which the function of the low-pass filter circuit 300 is turned on, the high-frequency noise is reduced by the low-pass filter circuit 300 even when the high-frequency noise is mixed into the video signal. Therefore, it is difficult for the noise detection circuit 302 to correctly detect that the high-frequency noise is mixed into the video signal. The filter control circuit 401 turns off the function of the low-pass filter circuit 300 in a period during which the noise detection circuit 302 detects that the high-frequency noise is mixed into the video signal. For example, the filter control circuit 401 turns off the function of the low-pass filter circuit 300 in the blanking period or a period during which the video signal is output from the optical black region in the imaging device 100.

As in the first embodiment, the noise detection circuit 302 compares the electric potential of one of the video signal in the blanking period and the video signal output from the optical black region in the imaging device 100 with a predetermined value. In this way, the noise detection circuit 302 determines whether the high-frequency noise is mixed into the video signal.

As in the first embodiment, the imaging control circuit 402 outputs timing information indicating one of a timing of the blanking period and a timing at which the video signal is output from the optical black region. The noise detection circuit 302 compares the electric potential of the video signal with the predetermined value at a timing indicated by the timing information.

When the high-frequency noise is detected by the noise detection circuit 302, the imaging control circuit 402 reduces the frame rate of the video signal in the imaging device 100 as in the first embodiment. Alternatively, when the high-frequency noise is detected by the noise detection circuit 302, the imaging control circuit 402 thins out a pixel from which a pixel signal is read in the imaging device 100 as in the first embodiment. By using one of these methods, the imaging control circuit 402 sets the signal-output time per one pixel of the imaging device 100 to a longer time than a predetermined time.

In a case in which the imaging control circuit 402 changes the frame rate of the video signal, the imaging control circuit 402 updates the timing information on the basis of the frame rate of the video signal as in the first embodiment.

The low-pass filter circuit 300 may be disposed in the operation unit 20 or the main body 40. In a case in which the low-pass filter circuit 300 is disposed in the operation unit 20, the video-signal receiver circuit 301 is disposed in the operation unit 20 or the main body 40. In a case in which the video-signal receiver circuit 301 is disposed in the operation unit 20, the noise detection circuit 302 is disposed in the operation unit 20 or the main body 40. In a case in which the video-signal receiver circuit 301 is disposed in the main body 40, the noise detection circuit 302 is disposed in the main body 40. In a case in which the low-pass filter circuit 300 is disposed in the main body 40, the video-signal receiver circuit 301 and the noise detection circuit 302 are disposed in the main body 40.

The low-pass filter circuit 300 may be configured such that the cut-off frequency fc of the low-pass filter circuit 300 is variable, and the noise detection circuit 302 may be changed to the noise detection circuit 302a shown in FIG. 3.

The filter control circuit 401 may set the cut-off frequency fc of the low-pass filter circuit 300 on the basis of the frequency of the high-frequency noise detected by the noise detection circuit 302a.

In the second embodiment, the endoscope system 1a can suppress deterioration of the waveform of the video signal as in the first embodiment.

Third Embodiment

Figure 5:
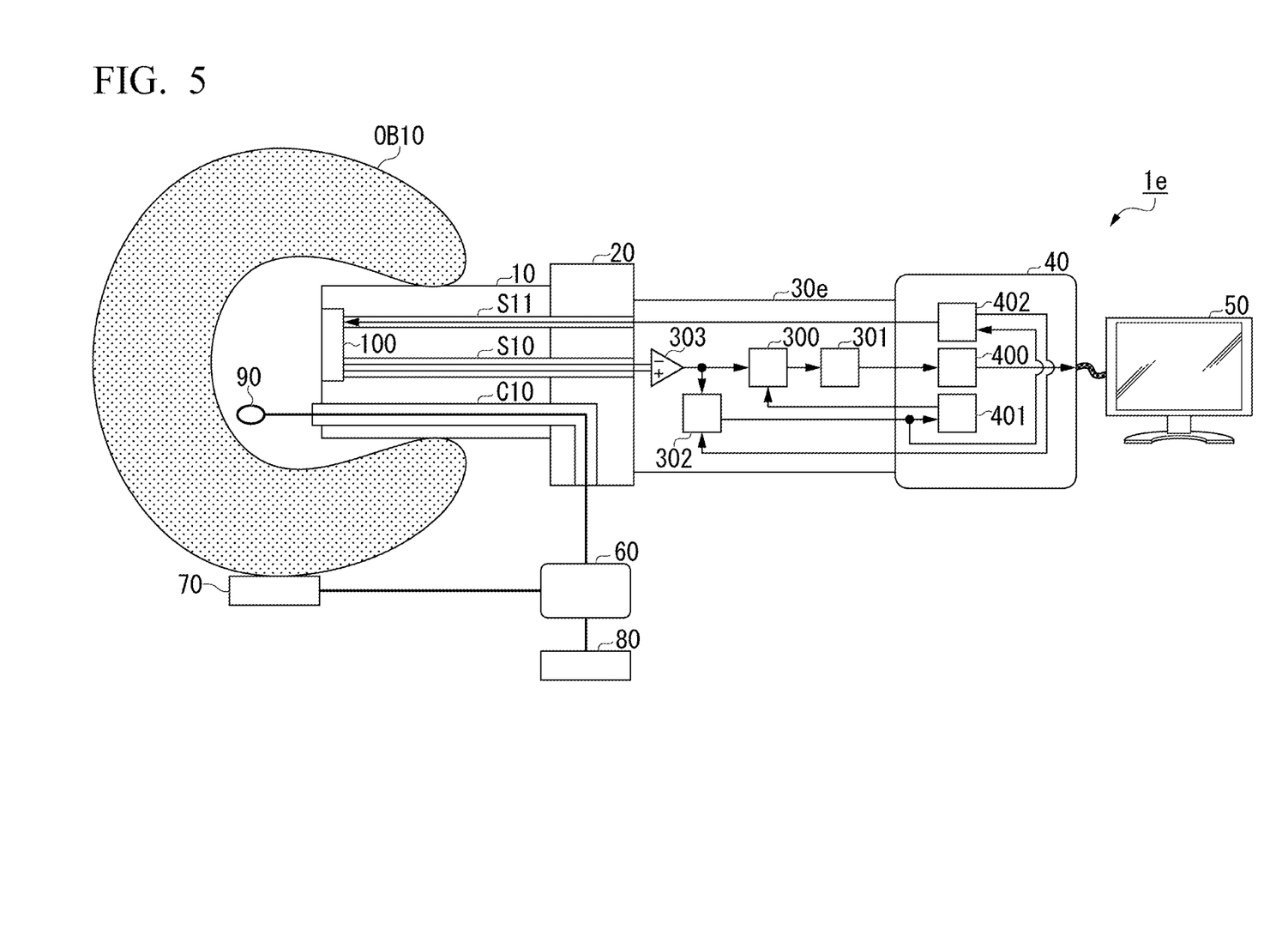
FIG. 5 is a block diagram showing a configuration of an endoscope system according to a third embodiment of the present invention.

FIG. 5 shows a configuration of an endoscope system 1e according to a third embodiment of the present invention. The same configuration as that shown in FIG. 1 will not be described.

In the third embodiment, the connection unit 30 shown in FIG. 1 is changed to a connection unit 30e. The connection unit 30e includes a low-pass filter circuit 300, a video-signal receiver circuit 301, a noise detection circuit 302, and a differential-signal receiver circuit 303.

In the third embodiment, the video signal is a differential signal including a first video signal and a second video signal having different electric potentials. The imaging device 100 outputs the first video signal and the second video signal to the signal line S10. The differential-signal receiver circuit 303 is electrically connected to the signal line S10. The differential-signal receiver circuit 303 receives the first video signal and the second video and converts the first video signal and the second video signal into a single-ended signal.

The low-pass filter circuit 300 is disposed between the differential-signal receiver circuit 303 and the video-signal receiver circuit 301 in a transmission path of the video signal. The single-ended signal output from the differential-signal receiver circuit 303 is input into the low-pass filter circuit 300. The low-pass filter circuit 300 reduces the high-frequency noise included in the single-ended signal.

The single-ended signal output from the differential-signal receiver circuit 303 is input into the noise detection circuit 302. The noise detection circuit 302 detects that the high-frequency noise is mixed into the single-ended signal before the single-ended signal passes through the low-pass filter circuit 300.

The low-pass filter circuit 300 may be configured such that the cut-off frequency fc of the low-pass filter circuit 300 is variable, and the noise detection circuit 302 may be changed to the noise detection circuit 302a shown in FIG. 3. The filter control circuit 401 may set the cut-off frequency fc of the low-pass filter circuit 300 on the basis of the frequency of the high-frequency noise detected by the noise detection circuit 302a.

In the third embodiment, the differential-signal receiver circuit 303 can eliminate noise mixed into the video signal by converting the first video signal and the second video signal into the single-ended signal. However, there is a possibility that the high-frequency noise remains in the single-ended signal generated by the differential-signal receiver circuit 303. The noise detection circuit 302 can detect the high-frequency noise remaining in the single-ended signal. In addition, the low-pass filter circuit 300 can reduce the high-frequency noise remaining in the single-ended signal.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope system, comprising:
an imaging device electrically connected to a signal line and configured to output a video signal to the signal line;
a receiver circuit electrically connected to the signal line and configured to receive the video signal;
a noise detection circuit configured to detect that noise having a higher frequency than a frequency of the video signal is mixed into the video signal;
a filter circuit having a function of reducing the noise included in the video signal;
an imaging control circuit configured to set a signal-output time per one pixel of the imaging device to a first set time when the noise is not detected by the noise detection circuit and set the signal-output time to a second set time longer than the first set time when the noise is detected by the noise detection circuit; and
a filter control circuit configured to turn off the function when the noise is not detected by the noise detection circuit and turn on the function when the noise is detected by the noise detection circuit.

2. The endoscope system according to claim 1,
wherein the noise detection circuit is configured to detect that the noise is mixed into the video signal that passes between the imaging device and the filter circuit.

3. The endoscope system according to claim 2,
wherein the noise detection circuit is configured to compare an electric potential of one of the video signal in a blanking period and the video signal output from an optical black region in the imaging device with a predetermined value so as to determine whether the noise is mixed into the video signal.

4. The endoscope system according to claim 3,
wherein the imaging control circuit is configured to output timing information indicating one of a timing of the blanking period and a timing at which the video signal is output from the optical black region, and
the noise detection circuit is configured to compare the electric potential of the video signal with the predetermined value at a timing indicated by the timing information.

5. The endoscope system according to claim 4,
wherein the imaging control circuit is configured to update the timing information on the basis of a frame rate of the video signal.

6. The endoscope system according to claim 2,
wherein the video signal is a differential signal including a first video signal and a second video signal having different electric potentials,
the receiver circuit is configured to convert the first video signal and the second video signal into a single-ended signal,
the filter circuit is configured to reduce the noise included in the single-ended signal, and
the noise detection circuit is configured to detect that the noise is mixed into the single-ended signal.

7. The endoscope system according to claim 1,
wherein the noise detection circuit is configured to detect that the noise is mixed into the video signal that has passed through the filter circuit.

8. The endoscope system according to claim 7,
wherein the noise detection circuit is configured to compare an electric potential of one of the video signal in a blanking period and the video signal output from an optical black region in the imaging device with a predetermined value so as to determine whether the noise is mixed into the video signal.

9. The endoscope system according to claim 8,
wherein the imaging control circuit is configured to output timing information indicating one of a timing of the blanking period and a timing at which the video signal is output from the optical black region, and
the noise detection circuit is configured to compare the electric potential of the video signal with the predetermined value at a timing indicated by the timing information.

10. The endoscope system according to claim 9,
wherein the imaging control circuit is configured to update the timing information on the basis of a frame rate of the video signal.

11. The endoscope system according to claim 7,
wherein the filter control circuit is configured to turn off the function in a period during which the noise detection circuit detects that the noise is mixed into the video signal.

12. The endoscope system according to claim 1,
wherein the imaging control circuit is configured to reduce a frame rate of the video signal in the imaging device so as to set the signal-output time to the second set time when the noise is detected by the noise detection circuit.

13. The endoscope system according to claim 1,
wherein the imaging device is configured to generate the video signal on the basis of a pixel signal that is read from each of two or more pixels that generate the pixel signals, and
the imaging control circuit is configured to thin out a pixel from which the pixel signal is read among the two or more pixels in the imaging device so as to set the signal-output time to the second set time when the noise is detected by the noise detection circuit.

14. The endoscope system according to claim 1,
wherein the noise detection circuit is configured to determine a frequency of the noise,
the filter circuit is configured such that a cut-off frequency thereof is variable, and
the filter control circuit is configured to set the cut-off frequency on the basis of the frequency determined by the noise detection circuit.

* * * * *